United States Patent [19]

Bey et al.

[11] 4,309,442

[45] Jan. 5, 1982

[54] METHOD FOR CONTROLLING FERTILITY IN MAMMALS

[75] Inventors: Philippe Bey, Strasbourg; Michel Jung, Illkirch Graffenstaden, both of France

[73] Assignee: Merrell Toraude et Compagnie, Strasbourg, France

[21] Appl. No.: 212,473

[22] Filed: Dec. 3, 1980

Related U.S. Application Data

[63] Continuation-in-part of Ser. No. 58,476, Jul. 18, 1979, abandoned, which is a continuation-in-part of Ser. No. 814,765, Jul. 11, 1977, abandoned.

[51] Int. Cl.³ .......................................... A61K 31/195
[52] U.S. Cl. .................................. 424/319; 424/311; 424/320
[58] Field of Search ...................... 424/311, 319, 320

[56] References Cited

U.S. PATENT DOCUMENTS 2,662,915  12/1953  Lontz et al. .................. 548/313 X
3,168,558  2/1965  Kurhajec et al. .............. 548/313 X

*Primary Examiner*—Leonard Schenkman
*Attorney, Agent, or Firm*—David E. Frankhouser

[57] ABSTRACT

A method for preventing gestation in mammals comprising the administration of a 2,5-diamino-2-halomethylpentanoic acid or derivative thereof.

8 Claims, No Drawings

METHOD FOR CONTROLLING FERTILITY IN MAMMALS

This application is a continuation-in-part of copending application Ser. No. 58,476, filed July 18, 1979, which is a continuation-in-part of application Ser. No. 814,765 filed July 11, 1977, both now abandoned.

This invention relates to the use of certain α-halomethyl ornithine derivatives as contragestational agents.

The use of pharmaceutical agents to prevent and suppress fertility among female mammals is well known to the medical arts. At present, the most widely accepted of these pharmaceutical agents comprises a mixture of steroidal estrogens and progestins. The administration of these agents establishes a type of pseudopregnancy thereby preventing normal ovulation from occurring in the female. Although quite effective, these agents are not without side effects. The most common side effects are similar to those symptoms observed during pregnancy including nausea, gastric disturbances, headache, dizziness, fluid retention, breast discomfort and vascular disorders.

Various intrauterine devices have also been employed for the prevention of pregnancy. These devices, however, are not totally effective, are occasionally expelled involuntarily and are often the cause of intrauterine irritation and/or bleeding.

The eradication of certain rodent and animal populations by means of poisons poses a danger to children and domestic animals. Moreover many of the methods presently employed in the control of fertility in domestic animals may involve non-reversible processes or may produce side effects during prolonged utilization, thereby limiting their usefulness.

Thus, there is a need for both new and better pharmaceutical agents for the prevention of pregnancy. In addition, there is a need for a safe and effective method to control animal and rodent populations which does not pose a potential danger to others.

The invention sought to be patented comprehends a method of preventing gestation in mammals which comprises the administration to said mammals of a contragestationally effective amount of a compound of the formula:

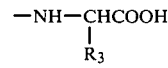

wherein:

Y is $FCH_2-$, $F_2CH-$, or $F_3C-$;

$R_a$ and $R_b$ are, independently, hydrogen, $(C_1-C_4)$alkylcarbonyl, or the group

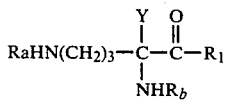

wherein $R_2$ is hydrogen, $(C_1-C_4)$alkyl, benzyl, or p-hydroxybenzyl; $R_1$ is hydroxy, $(C_1-C_8)$alkoxy, the group $-NR_4R_5$, wherein $R_4$ and $R_5$ are, independently, hydrogen, or, $(C_1-C_4)$alkyl, or the group

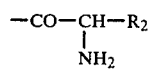

wherein $R_3$ is hydrogen, $(C_1-C_4)$ alkyl, p-hydroxybenzyl;

and the pharmaceutically acceptable salts and individual optical isomers thereof.

As used in Formula I, the term "$(C_1-C_4)$ alkylcarbonyl" means the group $-CO$-alkyl wherein the alkyl moiety has from 1 to 4 carbon atoms and is straight or branched, for example, methyl, ethyl, n-propyl, isopropyl, n-butyl, and isobutyl and tert-butyl. The term "$(C_1-C_4)$alky" means a straight or branched alkyl group having from 1 to 4 carbon atoms, such as methyl, ethyl, n-propyl, n-butyl, isopropyl and tert-butyl. The term "$(C_1-C_8)$ alkoxy" means an alkoxy group containing a straight or branched alkyl moiety having from 1 to 8 carbon atoms. Examples of $(C_1-C_8)$ alkoxy groups are methoxy, ethoxy, n-butoxy, n-pentyloxy, i-propoxy, and n-pentyloxy. Illustrative of acid addition salts of the compounds of the Formula I are the salts obtained with non-toxic organic or inorganic acids, such as hydrochloric, hydrobromic, sulfuric and phosphoric acids as well as acid metals salts such as sodium monohydrogen orthophosphate and potassium hydrogen sulfate. Illustrative organic acids which form suitable salts include mono, di and tricarboxylic acids, as for example, acetic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicyclic, 2-phenoxybenzoic and sulfonic acids, such as methane sulfonic acid and 2-hydroxyethane sulfonic acid. Such salts can exist in either a hydrated or a substantially anhydrous form.

Also included are non-toxic salts formed with any suitable inorganic or organic bases. Illustratively, these salts include those of the alkali metals, as for example, sodium and potassium; alkaline earth metals, such as calcium and magnesium; light metals of Group III A including aluminium; and organic primary, secondary and tertiary amines, as for example, trialkylamines, including N,N'-dibenzylethylenediamine, dihydroabiethylamine, N-(lower)alkylpiperidine, and other amines which are known by those skilled in the art to form non-toxic salts. These salts are prepared by conventional means and can exist in either a hydrated or a substantially anhydrous form.

Preferred embodiments of the compounds of Formula I are those wherein $R_1$ is hydroxy. More preferred embodiments are the compounds of Formula I wherein $R_1$ is hydroxy and Y is $FCH_2-$ or $F_2CH-$. Still more preferred embodiments are the compounds of Formula I wherein either $R_a$ or $R_b$ is hydrogen, $R_1$ is hydroxy, and Y is $-CH_2F$ or $-CHF_2$.

Preferred compounds of Formula I are 2,5-diamino-2-difluoromethylpentanoic acid ("α-difluoromethylornithine" or "α-DFMO") and 2,5-diamino-2-fluoromethylpentanoic acid ("α-monofluoromethylornithine or "α-MFMO").

It should be noted that the compounds of Formula I have an asymmetric center at the carbon atom which is alpha to the carboxyl group. Accordingly, the compounds may exist in either of their optical D or L-configurations or as their DL-racemates. As used herein the compounds are intented to be used as their racemic mixtures or as individual enantiomers.

The compounds of Formula I produce in vivo irreversible inhibition of ornithine decarboxylase (ODC), the enzyme which catalyzes the decarboxylation of ornithine to putrescine. The decarboxylation of ornithine to putrescine is the first step in the biosynthesis of the polyamines-spermidine and spermine. Spermidine is formed by the transfer of an activated aminopropyl moiety from S-adenosyl S-methyl homocysteamine to putrescine, while spermine is formed by the transfer of a second aminopropyl group to spermidine. S-adenosyl S-methyl homocysteamine is formed by the decarboxylation of S-adenosylmethionine (SAM), a reaction catalyzed by the enzyme S-adenosylmethionine decarboxylase (SAM-DC).

The polyamines, which are found in all animal tissues and microorganisms, are known to play an important role in cell growth and proliferation. The induction of cell growth and proliferation is associated with both a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in the testes, ventral prostate, and thymus; in neoplastic tissue; in psoriatic skin lesions; and in other cells undergoing rapid growth processes.

Since putrescine is a precursor of the polyamines, it is seen that blockade of the conversion of ornithine to putrescine, such as by inhibition of ODC, can provide a method for regulating the cellular levels of the polyamines.

It is well known that the early stages of embryogenesis are marked in particular by an increase in ODC activity and an elevation of polyamine levels [Russell et al, Proc. Natl. Acad. Sci. USA, 60, 1420 (1968) and Biochem. Biophys. Acta, 259, 247 (1972) and Manen et al, Dev. Biol., 57, 454 (1977)]. Hence, the polyamines may play an essential role in the maintenance of embryonic growth in mammals. It is believed that the compounds of Formula I may exert their contragestational effects by blocking the formation of the polyamines and thereby interrupting or arresting the course of early embryonic development. It should be understood, however, that the process of this invention is not meant to be limited by any particular theory or mode of action.

The contraceptive effects of the compounds of Formula I can be demonstrated in vivo in standard pharmacological tests in laboratory animals (e.g. female mice, rabbits, or rats). For example, female mice are mated and the test compound is given systemically daily throughout the period of gestation or throughout shorter periods thereof. The animals are killed and the uteri and their contents are examined for signs of pregnancy as evidenced by the number of viable developed foeti as compared to controls. When administered as a 2% solution in drinking water ad lib for 23 days, $\alpha$-DFMO-treated animals showed no viable developed foeti. In a similar experiment designed to locate the precise point during gestation when administration of an ODC inhibitor will produce its contragestational effect, $\alpha$-DFMO was administered as a 2% solution in drinking water to separate groups of mice on days 1-4, 5-8, 9-12, and 13-16 of gestation. Mice treated on days 5-8 displayed no signs of pregnancy, despite a positive indication of mating having been obtained, when autopsied on day 18 of gestation. Mice treated on days 1-4 and 9-12 contained fewer foeti, which were smaller than controls. Mice treated from days 13-16 differed from controls only in having smaller foeti. In an additional experiment groups of mice were injected subcutaneously with $\alpha$-DFMO 200 mg/kg every 6 hours on either day 5, 6, 7, 8, 9, or 10 of gestation. Two further groups received either 200 mg/kg or 500 mg/kg of $\alpha$-DFMO as the last dose on day 7 and the first dose on day 8. All the mice were autopsied on day 18 of gestation. The contragestational effects of $\alpha$-DFMO increased as the schedule of dosing approached day 8, and there was an abrupt loss of activity when treatment took place on days 9 or 10. Two injections of $\alpha$-DFMO, 200 mg/kg, on days 7 and 8 had marginal effects on gestation. Increasing the dose to 500 mg/kg, however, gave an effect approaching that seen following treatment with $\alpha$-DFMO, 200 mg/kg, four times on day 8 of gestation.

From the experiments herein-above described, it is seen that the period of gestation during which female mice are most susceptible to interruption of embryogenesis by administration of a compound of Formula I is between days 5 and 8, and in particular between days 7 and 8. This period lies between Standard Stage 8 and Standard Stage 16 of gestation, and in particular between Standard Stage 12 and Standard Stage 16. The Standard Stages of gestation for various species are defined by E. Witschi and are known in the art. [See Tables B 26-27, pages 82-92, Biology Data Book, Altman and Dittmer, Editors, Published by the Federation of American Societies for Experimental Biology, Washington, D.C., 1964, which is specifically incorporated herein by reference]. Thus, the critical period of gestation during which administration of an ODC inhibitor will provide a contragestational effect is between Standard Stage 8 and Standard Stage 16 of gestation, and, in particular, between Standard Stage 12 and Standard Stage 16, as defined by E. Witschi. The length of this period will vary with the species. In humans, for example, the period corresponding to Standard Stages 8 to 16 is between days 6 and 26 (after ovulation or fertilization) and the period corresponding to Standard Stages 12 and 16 is between days 19 and 27.

It will be apparent to those skilled in the art that, in order to achieve a contragestational effect, a compound of Formula I can be administered every day over an extended period of time without regard to the time of ovulation or fertilization, or it can be administered only during the critical period of gestation, as defined above, during which embryogenesis is most susceptible to intervention by an ODC inhibitor.

The inhibition of embryonic development in mice by $\alpha$-DFMO is discussed by J. Fozard et al, European Journal of Pharmacology, 65, 379 (1980), which is specifically incorporated herein by reference.

The compounds of Formula I wherein $R_1$ is hydroxy and each of $R_a$ and $R_b$ is hydrogen are prepared by treating an ester derivative of ornithine, wherein the amino groups are suitably protected, with a strong base to form the carbanion intermediate which is reacted with a suitable halomethyl-halo alkylating reagent in an aprotic solvent, such as, dimethylsulfoxide, dimethylformamide, dimethylacetamide, benzene, toluene, ethers, such as, tetrahydrofuran, diethyl ether or dioxane and in the presence of hexamethylphosphortriamide, when Y is other than $F_2CH-$, at a temperature of about $-120°$ C. to $120°$ C., preferably about $25°$ to $50°$ C. for about $\frac{1}{2}$ hour to 48 hours followed by acid or base hydrolysis as represented by the following reaction sequence.

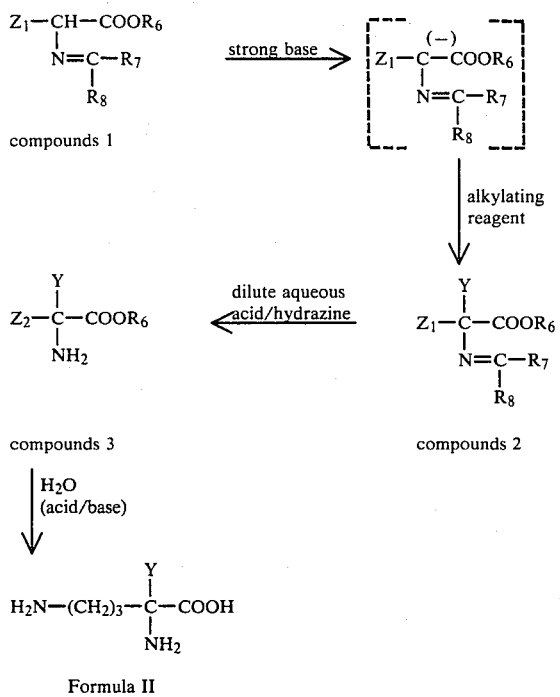

compounds 3

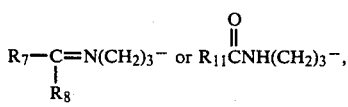

Formula II

In the above reaction sequence Y is $FCH_2-$, $F_2CH-$, or $F_3C-$; $R_6$ is ($C_1$-$C_4$) alkyl (for example, methyl, ethyl, isopropyl, n-propyl or n-butyl); $R_7$ is hydrogen, phenyl, alkyl, methoxy or ethoxy; $R_8$ is phenyl or ($C_1$-$C_8$) alkyl; or $R_7$ and $R_8$ taken together may form an alkylene group of from 5 to 7 carbon atoms, that is, $-CH_2-(CH_2)_m-CH_2-$ wherein m is an integer of from 3 to 5; $Z_1$ is $$R_7-\underset{\underset{R_8}{|}}{C}=N(CH_2)_3{}^- \text{ or } R_{11}\overset{\overset{O}{\|}}{C}NH(CH_2)_3{}^-,$$

wherein $R_7$ and $R_8$ are the same and have the meanings defined above, and is phenyl, benzyl, or $C_1$-$C_4$ alkyl (for example, methyl, ethyl or isopropyl) and $Z_2$ is $H_2N(CH_2)_3-$ or $R_{11}CNH-(CH_2)_3{}^-$ wherein $R_{11}$ has the above defined meanings. Illustrative examples of straight or branched ($C_1$-$C_8$) alkyl groups which $R_7$ and $R_8$ may represent, are, for example, methyl, ethyl, n-propyl, isopropyl, n-butyl, tert-butyl, n-pentyl, neopentyl or triethylmethyl.

Suitable strong bases which may be employed in the above reaction sequence to form the carbanion intermediate are those which will abstract a proton from the carbon atom alpha to the carboxy group, such as an alkyl lithium, for example, butyl lithium or phenyl lithium; lithium di-alkylamides, for example, lithium diisopropylamide; lithium amide; sodium or potassium t-butylate; sodium amide; metal hydrides, for example, sodium hydride or potassium hydride; tertiary amines, such as, triethylamine; lithium acetylide; or dilithium acetylide. Lithium acetylide, dilithium acetylide, sodium hydride, lithium diisopropylamide, and tertiary sodium butylate are particularly preferred bases.

Suitable alkylating reagents which may be employed in the above reaction sequence are illustratively chlorofluoromethane, bromofluoromethane, fluoroiodomethane, chlorodifluoromethane, bromodifluoromethane, difluoroiodomethane, bromotrifluoromethane, chlorotrifluoromethane, and trifluoroiodomethane. When chlorodifluoromethane, bromodifluoromethane, and difluoroiodomethane are used for the alkylative reaction, rapid addition of the halomethyl halo reagent to the carbanion intermediate derived from the compounds of Formula I necessary for optimal yields. The alkylating reagents are known in the art.

Removal of the protecting groups of the amine and carboxylic function may be achieved in one step by treatment of compounds 2 with aqueous acid, for example, hydrochloric acid or toluene sulfonic acid at a temperature of about 0° to 160° C. for about 4 to 24 hours to give compounds of Formula II. It is preferred to remove first the protecting groups of the amine function(s) of compounds 2 when said functions are protected as a Schiff's base by treating compounds 2 with dilute aqueous acid, for example, hydrochloric acid or with hydrazine or phenylhydrazine in solvents, such as, lower alcohols, for example, methanol or ethanol, ethers, chlorinated hydrocarbons, benzene and water. Removal of the protecting groups of the carboxylic functions and the amine groups when the amine groups are protected other than as a Schiff's base is achieved by treatment of compounds 3 with concentrated aqueous acids, for example, hydrobromic acid at a temperature of about 0° to 160° C. or in aqueous bases, for example, ammonium hydroxide.

The amine protected ester derivatives, that is, compounds 1, wherein $R_7$ is other than methoxy or ethoxy, are prepared by treating an appropriate amino acid ester with a carbonyl bearing compound to form a Schiff's base in a generally known manner, specifically: (a) when $R_7$ is hydrogen, by treating the appropriate amino acid ester with benzaldehyde or an alkanal having from 1 to 9 carbon atoms being straight or branched, for example, 1-propanal, 1-butanal, 2,2-dimethylpropan-1-al or 2,2-diethylbutan-1-al; (b) when $R_7$ is phenyl by treating the appropriate amino acid ester with benzophenone or phenyl alkyl ketone wherein the alkyl moiety has from 1 to 8 carbon atoms and is straight or branched, for example, phenyl methyl ketone, phenyl ethyl ketone, phenyl isopropyl ketone, phenyl n-butyl ketone or phenyl tert-butyl ketone; and (c) when $R_7$ is a straight or branched alkyl group having from 1 to 8 carbon atoms, treating the appropriate amino acid ester with a phenyl alkyl ketone as described above or with a di-alkyl ketone wherein each alkyl moiety has from 1 to 8 carbon atoms and is straight or branched, for example, dimethyl ketone, diethyl ketone, methyl isopropyl ketone, di-n-butyl ketone or methyl tert-butyl ketone. The carbonyl bearing compounds are known in the art or may be prepared by procedures well known in the art.

When in compounds 1 $R_7$ is methoxy or ethoxy, an appropriate amino acid ester derivative is reacted with benzoyl halide, for example, chloride, or an alkanoic acid halide, for example, chloride, wherein the alkanoic acid has from 1 to 9 carbon atoms and may be straight or branched, such as, acetyl chloride, propionyl chloride, butyryl chloride, tert-butyryl chloride, 2,2-diethylbutyric acid chloride or valeryl chloride, at 0° C. in ethers, methylenechloride, dimethylformamide, dimethylacetamide or chlorobenzene in the presence of an organic base such as triethylamine or pyridine after which the reaction mixture is allowed to warm to about 25° C. for one hour. The resulting amide derivative is combined with an alkylating reagent, such as, methylfluorosulfonate, dimethylsulfate, methyliodide, methyl p-toluenesulfonate or trimethyloxonium hexafluorophosphate when $R_7$ is methoxy or triethyloxonium tetrafluoroborate when $R_7$ is ethoxy at about 25° C. in a chlorinated hydrocarbon solvent such as methylene chloride, chlorobenzene or chloroform, and the reaction mixture is refluxed for about 12 to 20 hours. The mixture is then cooled at about 25° C. and an organic base such as triethylamine or pyridine is added after which the solution is extracted with brine and the product isolated.

When in compounds 1 $R_7$ and $R_8$ together form an alkylene group of from 5 to 7 carbon atoms said amino acid ester derivatives are obtained by treating the amino acid ester with a cyclic alkanone selected from cyclopentanone, cyclohexanone and cycloheptanone to form a Schiff's base by procedures generally known in the art.

When in compounds 1, $Z_1$ is

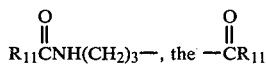

protecting group is added to ornithine by treatment of said amino acid with an excess of copper salt, for example, copper carbonate in boiling water for about 1 to 6 hours, and upon cooling to room temperature the insoluble materials are filtered off, and the filtrate is treated with an appropriate acid halide, for example, in acetone in the presence of a base such as sodium bicarbonate or sodium hydroxide followed by treatment with hydrogen sulfide. Illustrative acid halides which may be employed are acetyl chloride, propionyl chloride, benzoyl chloride or 2-phenylacetyl chloride.

The amino acid ester is formed by generally known procedures, for example, the amino acid is treated with an appropriate alcohol, such as, methanol, ethanol, or n-butanol saturated with HCl gas.

The compounds of Formula I wherein $R_a$ and $R_b$ are hydrogen, $R_1$ is hydroxy, and Y is —CH$_2$F or —CHF$_2$ can be made by an alternative method, which is illustrated herein by Example 10 which describes the preparation of 2,5-diamino-2-fluoromethylpentanoic acid ($\alpha$-monofluoromethyl ornithine or $\alpha$-MFMO). $\alpha$-DFMO can be prepared by an obvious modification of this process employing difluoroacetonitrile in place of fluoroacetonitrile.

Following is described the preparation of compounds of Formula I wherein $R_a$ and/or $R_b$ are other than hydrogen. The following description is applicable to all the above said compounds, however, it is necessary to protect one or the other of the amino groups prior to treatment with the appropriate reactant, that is, acid halide or anhydride, alkyl haloformate or acid of the formula

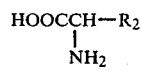

or anhydride thereof as described below to give compounds wherein either or both of $R_a$ and $R_b$ is other than hydrogen as follows: when $R_a$ is hydrogen and $R_b$ is other than hydrogen, the amino group to which $R_b$ is attached is protected as a copper salt by treatment of the corresponding derivative wherein $R_a$ and $R_b$ are hydrogen with an excess of a copper salt, for example, copper carbonate after which the amino group to which $R_a$ is attached is protected with, for example, benzyloxycarbonyl or tert-butoxycarbonyl by treatment with benzyl chloroformate or tert-butoxycarbonyl azide respectively followed by treatment with hydrogen sulfide, by procedures generally known in the art and illustrated more fully in the specific examples contained herein, prior to treatment with the appropriate reactant described below to give compounds wherein $R_b$ is other than hydrogen. The $R_a$ amine protecting group is subsequently removed by treatment with acid, for example, trifluoroacetic acid, HBr in dioxane or HBr in acetic acid or hydrogenolysis. The thus obtained compounds, that is, compounds wherein $R_a$ is hydrogen and $R_b$ is other than hydrogen may be treated with the appropriate reactants described below to give compounds wherein $R_a$ and $R_b$ are both other than hydrogen and may be the same or different. In preparing compounds wherein $R_a$ is other than hydrogen and $R_b$ is hydrogen the amino group to which $R_b$ is attached is protected as a copper salt by treatment of the corresponding derivative wherein each $R_a$ and $R_b$ is hydrogen with an excess of copper salt, for example, copper carbonate prior to treatment with the appropriate reactant described below followed by acid or base hydrolysis and subsequently treating with hydrogen sulfide.

The compounds of Formula I wherein $R_a$ or $R_b$ is alkylcarbonyl wherein the alkyl moiety is straight or branched and has from 1 to 4 carbon atoms are prepared by treating the corresponding derivatives wherein $R_a$ or $R_b$ is hydrogen or is suitably protected or as to compounds of Formula I, $R_a$ is other than hydrogen as described above and $R_1$ is hydroxy with an acid halide of the formula

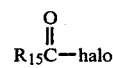

wherein halo is a halogen atom, for example, chlorine or bromine and $R_{15}$ is a straight or branched alkyl group having from 1 to 4 carbon atoms or an appropriate acid anhydride, in water in the presence of a base such as sodium hydroxide or sodium borate at a temperature of about 0° to 25° C. for about ½ hour to 6 hours. When appropriate, protecting groups are removed as described hereinabove by treatment with acid or hydrogenolysis.

The compounds of Formula I wherein $R_a$ or $R_b$ is

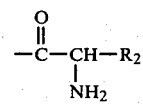

wherein $R_2$ is hydrogen, a straight or branched lower alkyl group of from 1 to 4 carbon atoms, benzyl or p-hydroxybenzyl and $R_1$ is hydroxy are prepared by treating the corresponding derivative wherein $R_a$ or $R_b$ is hydrogen or is suitably protected or as to compounds of Formula I, $R_b$ is other than hydrogen as described hereinabove with an acid of the formula $$\text{HOOC}-\underset{\underset{\text{NH}_2}{|}}{\text{CH}}-\text{R}_2,$$

or an anhydride thereof, wherein the amino group is protected with a suitable blocking group such as benzyloxycarbonyl or tert-butoxycarbonyl and $R_2$ has the meaning defined hereinabove in an ether, such as, tetrahydrofuran or dioxane, methylene chloride or chloroform and in the presence of a dehydrating agent, such as, dicyclohexylcarbodiimide when the free acid is employed, at a temperature of about 0° to 35° C. for about 1 to 12 hours followed by acid and base hydrolysis and when appropriate, hydrogenolysis to remove the protecting groups.

The compounds of the Formula I wherein $R_1$ is a straight or branched alkoxy group of from 1 to 8 carbon atoms are prepared by converting the corresponding compounds wherein $R_1$ is hydroxy to the acid halide by, for example, treatment with thionyl chloride, followed by alcoholysis with an alcohol of the formula $R_{17}OH$ wherein $R_{17}$ is a straight or branched alkyl group having from 1 to 8 carbon atoms by procedures generally known in the art. Alternatively, compounds of Formula I wherein $R_1$ is a straight or branched alkoxy group of from 1 to 8 carbon atoms may be prepared from the corresponding derivative wherein $R_1$ is hydroxy by treatment of said derivative with an alcohol of the formula $R_{17}OH$ as defined above saturated with HCl for about 30 minutes for 12 hours at a temperature of about 25° C. to the boiling point of the alcohol.

The compounds of this invention wherein $R_1$ is $-NR_4R_5$ wherein each of $R_4$ and $R_5$ is hydrogen or a lower alkyl group of from 1 to 4 carbon atoms are prepared by an acylation reaction of an acid halide, for example, an acid chloride, of the corresponding compound wherein $R_1$ is hydroxy and $R_a$ and $R_b$ have the meanings defined in Formula I with the proviso that any free amino group is suitably protected with groups, such as, carbobenzyloxy or tert-butoxycarbonyl with an excess of an appropriate amine which may be represented as $HNR_4R_5$. The reaction is carried out in methylene chloride, chloroform, dimethyl formamide, or ethers such as tetrahydrofuran and dioxane, or benzene at about 25° C. for about 1 to 4 hours. Suitable amines are ammonia, or a compound which is a potential source of ammonia, for example, hexamethylenetetramine; primary amines, for example, methylamine, ethylamine or n-propylamines; and secondary amines, for example, dimethylamine, diethylamine or di-n-butylamine. Following the acylation reaction the protecting groups are removed by treatment with acid, for example, trifluoroacetic acid or hydrogen bromide in dioxane.

The compounds of Formula I wherein $R_1$ is $$-\underset{\underset{R_3}{|}}{\text{NH}}-\text{CH}-\text{COOH}$$

are prepared by reacting the corresponding derivative wherein $R_1$ is hydroxy or a functional derivative thereof, such as, an acid anhydride and $R_a$ and $R_b$ have the meanings defined in Formula I with the proviso that any free amino group is protected with a suitable blocking group, such as, benzyloxycarbonyl, tert-butoxycarbonyl by reacting the amine protected free acid with a compound of the structure $$\text{NH}_2-\underset{\underset{R_3}{|}}{\text{CH}}-\text{COOR}_{18}$$

wherein $R_3$ has the meaning defined in Formula I and $R_{18}$ is a lower alkyl group, for example, methyl or ethyl in an ether solution, such as, tetrahydrofuran or dioxane at about 0° C. to 35° C. for about 1 to 20 hours followed by acid then base hydrolysis, for example, with 2 N aqueous $NH_3$ at about 0° to 50° C. for about 1 to 20 hours, to remove the protecting group(s), with the proviso that when the amine protected free acid is employed the reaction is carried out using a dehydrating agent such as dicyclohexylcarbodiimide.

The lactams of the compounds of Formula I wherein each of $R_a$ and $R_b$ is hydrogen and $R_1$ is hydroxy are prepared from the corresponding amino acid ester of the structure:

$$\text{H}_2\text{N(CH}_2)_n-\underset{\underset{\text{NH}_2}{|}}{\overset{\overset{Y}{|}}{C}}-\text{COR}_{19} \qquad \text{Formula III}$$

wherein n and Y have the meanings defined in Formula I, and $R_{19}$ is a straight or branched alkoxy group of from 1 to 8 carbon atoms, illustratively methoxy, ethoxy, isopropoxy, butoxy or hexyloxy, by treating said amino acid esters with an appropriate base, such as, sodium hydroxide, potassium hydroxide, lithium hydroxide, sodium carbonate, potassium carbonate, sodium methoxide, potassium methoxide, potassium tert-butoxide, sodium amide, or an organic amine such as a trialkylamine, for example, triethylamine in a solvent such as a lower alcohol, for example, methanol, ethanol, isopropyl alcohol, n-butanol, water, dimethylformamide, dimethylsulfoxide, hexamethylphosphortriamide or mixtures of these solvents for from ½ hour to 24 hours at a temperature of from about 0° to 120° C. optionally under a nitrogen atmosphere.

The compounds of Formula III are obtained by procedures generally known in the art from the corresponding amino acid, for example, by treating said amino acid with an appropriate alcohol, for example, methanol, ethanol, isopropyl alcohol, n-butanol or n-heptanol saturated with HCl gas.

The individual optical isomers of the compounds of Formula I wherein each of $R_a$ and $R_b$ is hydrogen and $R_1$ is hydroxy are obtained from the lactam of said compounds using a (+) or (−) binaphthylphosphoric acid salt by the method of R. Viterbo et al, Tetrahedron Letters, 48, 4617 (1971). Other resolving agents such as (+) camphor-10-sulfonic acid may also be employed. The individual optical isomers of compounds of Formula I wherein R is other than hydrogen and $R_1$ is other than hydroxy are obtained as described herein for the racemate only starting with the resolved free amino acid.

In practicing this invention, the compounds of Formula I, or their pharmaceutically acceptable salts, can be conveniently administered in a variety of ways depending upon the mamal to be treated. Thus in humans, the compound can be administered in various dosage unit forms such as tablets, capsules, powders, emulsions, suspensions and various parenteral preparations suitable for intramuscular, intravenous or subcutaneous preparations. Due to the rapid absorption and excretion of these particular drugs, and due to the relatively short half life of the drug in vivo, sustained release preparations may be of particular importance in the practise of this invention. Additionally, since the compounds do not produce an antifertility effect in males, they can be nonselectively administered in non-human mammals via baits, feeds or drinking water.

Illustrative of the term mammals as used herein are rodents, such as mice, rats, guinea pigs, shrews, squirrels, and rabbits, and other warm-blooded mammals, such as ferrets, dogs, cats, cows, horses and primates, including man.

The drug is most advantageously administered as a pharmaceutical composition in conjunction or admixture with additional organic or inorganic pharmaceutical excipients. Suitable solid excipients include inert diluents, for example, calcium carbonate, sodium carbonate, lactose, calcium phosphate or sodium phosphate; granulating and disintegrating agents, as for example, maize starch or alginic acid; binding agents, as for example, various starches, gelatin, lactose or acacia mucilage, and lubricating agents, such as magnesium stearate, stearic acid or talc. Suitable liquid excipients include water and alcohols, such as ethanol, benzyl alcohol and the polyethylene alcohols, either with or without the addition of a surfactant. In general, the preferred liquid excipients, particularly for injectable preparations include water, saline solution, dextrose and glycol solutions such as aqueous propylene glycol solutions such as aqueous propylene glycol or an aqueous solution of polyethylene glycol. Liquid preparations to be used as sterile injectable solutions will ordinarily contain from about 0.1% to about 25% by weight and preferably from about 0.1% to about 10% by weight of the active ingredient in solution.

A preferred method of administration is oral, either in a solid dose form such as a tablet or capsule, or in a liquid dose form such as an elixir, suspension, emulsion or syrup. Ordinarily, the active ingredient comprises from about 0.5% to about 100% by weight of an oral composition. In such compositions the pharmaceutical carrier is generally aqueous in nature, as for example, aromatic water, a sugar-based syrup or a pharmaceutical mucilage. Suspending agents may be added as well as agents to control the viscosity, as for example, magnesium aluminum silicate or carboxymethylcellulose. Buffers, preservatives, emulsifying agents and other excipients can also be added.

Formulations for oral use may be presented as hard or soft shell gelatin capsules containing only the active ingredients in admixture with a solid diluent, as for example lactose, sorbitol, calcium carbonate, calcium phosphate or kaolin. Sustained release tablets or capsules are of particular use in providing a steady and constant supply of the drug to the mammal being treated. Thus, the compound of this invention may be coated as slow release beads or granules and placed in capsules or compressed into tablets. Tablets can also be prepared having multiple layers containing slow-release material or slow-release cores. Suitable coatings include polyvinyl alcohol, polyvinyl acetate, hydroxyethyl cellulose, hydroxypropyl cellulose, cellulose acetate phthalate and hydroxypropyl methylcellulose phthalate.

For parenteral administration such as intramuscular, intravenous or subcutaneous administration, the proportion of active ingredient ranges from about 0.05% to about 20% by weight, and preferably from about 0.1% to about 10% by weight of the liquid composition. In order to minimize or eliminate irritation at the site of injection, such compositions may contain a nonionic surfactant having a hydrophilelipophile balance (HLB) of from about 12 to about 17. The quantity of surfactant in such formulations ranges from about 1% to about 15% by weight. The surfactant can be a single component having the above-identified HLB, or a mixture of two or more components having the desired HLB. Illustrative of surfactants useful in parenteral formulations are the class of polyoxyethylene sorbitan fatty acid esters and the high molecular weight adducts of ethylene oxide with a hydrophobic base, formed by the condensation of propylene oxide with propylene glycol.

The amount of active ingredient that is administered varies over a wide range depending upon the size, age or the particular mode of administration employed, and can be any amount that is sufficient to prevent gestation in the particular species of mammal being treated. Thus, a particular dosage unit may contain from as little as 50 mg to as much as 750 mg of the active ingredient and can be administered in multiple dosages one or more times per day during the period in which the antifertility effect is desired. As a prophylactic agent for the prevention of gestation in non-human mammals, the drug can be administered as a 0.125% to 4.0% solution in drinking water or the corresponding amount added to the animal's feed. Preferably, a 2.0% solution of the drug in drinking water is employed.

The pharmaceutical compositions can be administered to mammals at a daily dose ranging from about 10 mg/kg to 1 g/kg of body weight. Preferably, a dosage of from 10 mg/kg to 100 mg/kg, body weight, is administered one or more times per day as necessary. Illustratively, a typical human dose would be in the form of one or more 500 mg tablets administered every 6 hours.

The following Examples illustrate the preparation of the compounds of Formula I, the preparation of certain pharmaceutical compositions suitable for oral administration, and the antifertility effects obtained upon administration of an illustrative compound to male and female mice or rats.

EXAMPLE 1

Dibenzaldimine Ornithine Methyl Ester

L-ornithine hydrochloride, 18 kg and 90 l of methanol are stirred at room temperature to obtain a reasonably uniform suspension. Hydrogen chloride gas is added to this suspension first passing into solution and then precipitating as the ester dihydrochloride. The introduction of hydrogen chloride is stopped and the reaction mixture is refluxed for one hour. Upon cooling to 5° C. for 3 hours, the ornithine methyl ester dihydrochloride is collected by filtration, washed with cold methanol, and vacuum dried at room temperature, yielding approximately 21.4 kg of material.

Approximately 6.8 kg of ornithine methyl ester dihydrochloride is suspended in 10 l of methylene chloride, cooled to 0° C. and 6.5 kg of benzaldehyde, dissolved in 10 l of methylene chloride, is added at such a rate as to maintain the reaction temperature at 0° to −5° C. The reaction mixture is allowed to warm to room temperature, stirring continued for an additional 2 hours, and 20 l of diethyl ether added thereto. Upon standing overnight, the triethylammonium hydrochloride that precipitates is removed by filtration, and the precipitate is washed with an additional 6.8 liters of diethyl ether. The combined filtrates are evaporated in vacuo and the residue dissolved in 34 l of diethyl ether. The organic solution is washed four times with 4 l of water, dried over anhydrous sodium sulfate, filtered and evaporated in vacuo to yield 9.28 kg of dibenzaldimine ornithine methyl ester as an oil.

EXAMPLE 2

2,5-Diamino-2-difluoromethylpentanoic acid (α-DFMO)

Tetrahydrofuran, 15 liters, are cooled to a temperature of $-80°$ C. by the introduction of liquid nitrogen. Di-isopropylamine, 2.82 liters, is added under an atmosphere of nitrogen and twelve liters of a 15% solution of n-butyllithium, which is dissolved in hexane, is added to this mixture at such a rate as to maintain the temperature of the mixture at $-75°$ to $-80°$ C. To this mixture, still under nitrogen, is added 5.12 kg of dibenzaldimine ornithine methyl ester dissolved in 15 liters of tetrahydrofuran at such a rate that the reaction temperature remains between $-75°$ and $-80°$ C. The temperature of the reaction mixture is gradually increased to approximately 35° or 40° C. and maintained at that temperature under nitrogen for one hour. The nitrogen gas is replaced and approximately 13 kg of chlorodifluoromethane gas (Freon®22) is added at such a rate as to maintain the reaction mixture at a temperature of 40° to 50° C. To this mixture is added 20 l of an aqueous saturated chloride and 75 l of diisopropyl ether. The organic layer is separated and the aqueous layer extracted with 25 l of diisopropyl ether. The organic extracts are combined, washed four times with 20 l of aqueous saturated sodium chloride, dried over anhydrous sodium sulfate, filtered, and the filtrate evaporated in vacuo to an oil.

The oil residue is hydrolyzed with 30 l of 1 N-hydrochloric acid at room temperature for 3 hours, and reaction mixture is extracted three times with 5 l of chloroform. The combined aqueous layers are stirred for 15 hours at room temperature with 30 l of 10 N hydrochloric acid. The reaction mixture is extracted three times with 5 l of chloroform and the aqueous layer separated and evaporated in vacuo, diluted with 8 l of water and evaporated again in vacuo to remove the major portion of the acid present. The residue is diluted with 6 l of water and triethylamine added to a pH of 3.3. Charcoal, 100 g, is added to the mixture and the mixture warmed to 60°–70° C. for two hours. The mixture is filtered, washed with two liters of water and 80 l of acetone added to the filtrate. Upon standing overnight, the crude α-difluoromethylornithine which is obtained (2.1 kg) is filtered and washed with 2 liters of ethanol. Two recrystallizations of a portion of this crude material from a water-ethanol mixture yields 2,5-diamino-2-difluoromethylpentanoic acid, m.p. 183° C.

EXAMPLE 3

3-Amino-3-difluoromethyl-2-piperidone

To a solution of methyl-2-difluoromethyl-2,5-diaminopentanoate-dihydrochloride (2.7 g) in dry methanol (30 ml) is added under nitrogen 2 equivalents of sodium methylate in methanol (0.46 g of sodium in 20 ml of methanol). The reaction mixture is stirred for 3 hours at room temperature then the solvent is evaporated under reduced pressure. The residue is extracted with ether to yield crude 3-amino-3-difluoromethyl-2-piperidone which is purified either by crystallization from $CHCl_3$/pentane: (mp: 149° C.) or by distillation (bp: 135° C./0.05 mmHg).

EXAMPLE 4

(−) and (+) 2-Amino-3-difluoromethyl-2-piperidone hydrochloride

To a solution of (−) binaphthylphosphoric acid (BNPA) (1.27 g) in hot ethanol (50 ml) is added a solution of (±) 3-amino-3-difluoromethyl-2-piperidone (0.546 mg) in hot ethanol (5 ml). On cooling, crystals separate. The reaction mixture is then let stand at 4° C. overnight. The precipitate is filtered off, washed with ethanol and diethyl ether to give 0.54 g of (−) binaphthylphosphoric salt ($[α]_D = -409°$ C. = 0.3, MeOH mp: 300° C.). Recrystallization of the mother liquor yields 0.15 g of (−) binaphthylphosphoric salt. Concentration of the filtrate gives 1.1 g of a sticky material which is trated with HCl 3 M at room temperature for 3 hours. The (−) BNPA is filtered off and the filtrate concentrated under reduced pressure. Recrystallization of the residue (320 mg) in ethanol affords (+) 3-amino-3-difluoromethyl-2-piperidonemonohydrochloride (160 mg) ($[α]_D = +18°6$, C=1, MeOH mp 238° C.). Treated in the same condition the (−) BNPA salt (436 mg) gives (−) 3-amino-3-difluoromethyl-2-piperidone monohydrochloride (137 mg) which is recrystallized in ethanol (67 mg) ($[α]_D = -19°$, C=1.02, MeOH; mp=240° C. dec.).

(−) and (+) 2-difluromethyl-2,5-diamino pentanoic acid monohydrochloride (−) 3-Difluoromethyl-3-amino-2-piperidone hydrochloride (60 mg) is heated in HCl 6 M (4 ml) at reflux for 12 hours. After concentration under reduced pressure, the residue is dissolved in water and the pH of the solution is adjusted to 4.5 with a solution of $NEt_3$. The solution is then concentrated under reduced pressure and the residue extracted many times with chloroform and then recrystallized from $H_2O$/EtOH to give (+) 2-difluoromethyl-2,5-diamino pentanoic acid monohydrochloride (54 mg) ($[α]_D = +6°$, C=0.48; MeOH; mp≧240° C.). By an identical treatment, (+) 3-difluoromethyl-3-amino-2-piperidone hydrochloride (96 mg) gives (−) 2-difluoromethyl-2,5-diaminopentanoic acid monohydrochloride (56 mg) ($[α]_D = -10°$, C=0.7 MeOH, mp≧224°).

EXAMPLE 5

2,5-Diamino-2-difluoromethylpentanoic acid

Under nitrogen a solution (500 ml) of 2 M butyllithium in hexane is added to a stirred solution of 143.1 ml of diisopropylamine in 1.5 liters of tetrahydrofuran at −78° C. after which 261 g (0.81 mole) of ornithine dibenzylaldimine methyl ester in 1.5 l of tetrahydrofuran is added. Upon completion of the addition the reaction temperature is raised to 40° C. and maintained between 40° and 50° C. for 3 hours during which time chlorodifluoromethane gas is bubbled through the mixture with stirring. The reaction mixture is then treated with a saturated solution of sodium chloride. The organic material is extracted with ether, and the ether extract washed several times with sodium chloride solution, dried over magnesium sulfate and evaporated to give a viscous oil. The oil is stirred with 1 N HCl (1.5 l)

for 3 hours, the mixture extracted several times with chloroform and the aqueous solution evaporated to dryness. The oily residue is refluxed with 12 N hydrochloric acid (1.5 l) for 16 hours, the cooled solution clarified by chloroform extraction before concentration, decolorization (charcoal), and further concentration to about 750 ml. The pH of the solution is adjusted to 3.5 by the addition of triethylamine, the solution treated again with charcoal before concentration to about 500 ml and dilution with 7–8 l of acetone. The precipitated product is filtered off and washed with ethanol. The crude product is recrystallized by dissolving in about 150 ml hot water and treatment of the solution with hot ethanol (450 ml). On cooling crystals of 2,5-diamino-2-difluoromethylpentanoic acid hydrochloride monohydrate separate; 71 g (37%), m.p. 183° C.

EXAMPLE 6

2-Amino-5-benzyloxycarbonylamino-2-difluoromethylpentanoic acid

To a solution of the copper salt of 2-difluoromethyl-2,5-diaminopentanoic acid in water, prepared by reacting 2-difluoromethyl-2,5-diaminopentanoic acid monohydrate hydrochloride (2.4 g) with copper carbonate (6 g), is added slowly at 0° C. with stirring 1.1 g of benzylchloroformate. The reaction mixture is stirred for an additioal 3 hours at room temperature after which hydrogen sulfide is passed through the solution until it becomes colorless. The precipitate is filtered off, and the pH of the aqueous solution is adjusted to 6 by the addition of hydrochloric acid. Upon concentration 2-amino-5-benzyloxycarbonylamino-2-difluoromethylpentanoic acid is obtained.

By the above procedure only using tert-butoxycarbonylazide, acetylchloride or benzoylchloride in place of benzylchloroformate gives respectively 2-amino-5-tert-butoxycarbonylamino-2-difluoromethylpentanoic acid, 5-acetylamino-2-amino-2-difluoromethylpentanoic acid and 2-amino-5-benzyloxycarbonyl-2-difluoromethylpentanoic acid.

EXAMPLE 7

2-Acetylamino-5-amino-2-difluoromethylpentanoic acid

To a solution of 2.9 g of 2-amino-5-tert-butoxycarbonylamino-2-difluoromethylpentanoic acid in 10.5 ml of 1 M sodium hydroxide is added at 0° C. simultaneously 0.19 g of acetylchloride and 5 ml of 2 M aqueous sodium hydroxide. The reaction mixture is stirred for 3 hours at room temperature. The alkaline aqueous solution is then adjusted to a pH of 2 with hydrochloric acid and extracted with ethylacetate. After usual work-up the solvent is evaporated and the residue taken up in trifluoroacetic acid. After concentration and purification by ion exchange chromatography on a resin 5-amino-2-acetylamino-2-difluoromethylpentanoic acid is obtained.

EXAMPLE 8

5-Amino-2-difluoromethyl-2-(2-aminopropionylamino)-pentanoic acid

To a solution of 3.2 g of 2-amino-5-benzyloxycarbonylamino-2-difluoromethylpentanoic acid in 10 ml of 1 M aqueous sodium hydroxide is added at 0° C. simultaneously a solution of tert-butoxycarbonylazide, prepared from 3 g of tertbutoxycarbonylhydrazine, and a solution of 5.5 ml of 2 M aqueous sodium hydroxide. The reaction mixture is stirred overnight then extracted twice with 50 ml of ether. The alkaline aqueous solution is then adjusted to a pH of 2 with hydrochloric acid and extracted with ethylacetate. Usual work-up gives a solid residue which is dissolved in 15 ml of dry dimethylformamide and treated at room temperature with 1.6 g of benzylbromide in the presence of 2 ml of dicyclohexylamine. The reaction mixture is stirred for 14 hours and then the precipitate is filtered off. The filtrate is evaporated under reduced pressure. The resulting residue is partitioned between 100 ml of ethylacetate and water. The organic phase is washed successively with 20 ml of 1 normal aqueous hydrochloric acid, 20 ml of water, 20 ml of 5% aqueous sodium bicarbonate, 20 ml of water and 50 ml of brine then dried over magnesium sulfate. The solvent is evaporated and the residue taken up in 10 ml of trifluoroacetic acid. After 1 hour at room temperature the excess trifluoroacetic acid is stripped off under reduced pressure and the residue is taken up in a saturated solution of sodium bicarbonate and extracted with 50 ml of ether. The ether phase is dried over magnesium sulfate and then added at 0° C. to a solution of N-benzyloxycarbonyl-O-ethoxycarbonylalanine (2 g) in 20 ml of ether. Stirring is continued overnight at room temperature. The solvent is evaporated and the resulting syrupy residue is taken up in glacial acetic acid (20 ml) and hydrogenated over Pd/C 10% (200 mg). After completion of the hydrogen uptake the catalyst is filtered off. The filtrate is concentrated under reduced pressure with toluene and the residue purified by ion exchange chromatography on an acidic resin to give 5-amino-2-(2-aminopropionylamino)-2-difluoromethylpentanoic acid.

EXAMPLE 9

2-[(2,5-Diamino-2-difluoromethyl-1-oxopentane)amino]-propionic acid

To a solution of 2,5-diamino-2-difluoromethylpentanoic acid monohydrate hydrochloride (2.35 g) in 10 ml of 2 M aqueous sodium hydroxide is added at 0° C. simultaneously a solution of 10 ml of 2 molar aqueous sodium hydroxide and a solution of tert-butoxycarbonylazide prepared from 3 g of tert-butoxycarbonylhydrazine. The reaction mixture is stirred overnight at room temperature and then extracted twice with 250 ml portions of ether. The alkaline aqueous solution is adjusted to a pH of 2 with hydrochloric acid and extracted with ethylacetate. After usual work-up the solvent is evaporated and the residue taken up in 40 ml of dry ether. After addition is 1 g of triethylamine an ether solution of 1 g of ethylchloroformate is added slowly at 0° C. with stirring. The precipitate is filtered off and the ether solution is added at once to a solution of alanine tert-butylester (1.5 g). Stirring is continued overnight and the solvent is evaporated. The residue is taken up in trifluoroacetic acid. After concentration and purification by ion exchange chromatography on an Amberlite IR 120 resin 2-[(2,5-diamino-2-difluoromethyl-1-oxopentane)amino]-propionic acid is obtained.

EXAMPLE 10

2-Fluoromethyl-2,5-diaminopentanoic acid (α-MFMO)

A. 2-Fluoromethyl-2-amino-5-methoxy-valeronitrile

Under an atmosphere of nitrogen, 3-methoxypropyl magnesium chloride is prepared from 3-methoxy-1- chloropropane (5.43 g, 50 mmol, prepared according to Haworth and Perkin, Chem. Zentralblatt II 1271 (1912) and magnesium turnings (1.22 g, 50 mmol) in dry THF (50 ml). The mixture is heated under reflux for 3 hours, then cooled to −30° C. and a solution of fluoroacetonitrile (2.95 g, 50 mmol) in THF (30 ml) is added during 20 minutes. After keeping the mixture at −30° C. for ½ hour more, a solution of sodium cyanide (4.9 g, 100 mmol) and ammonium chloride (8.09 g, 150 mmol) in water (100 mL), previously cooled to 0° C., is added and the mixture is stirred for ¾ hours at room temperature. After saturating with sodium chloride, the THF layer is separated and the aqueous phase is extracted twice with ether. After drying ($Na_2SO_4$), the combined organic extracts are evaporated to give 2-fluoromethyl-2-amino-5-methoxyvaleronitrile (4.0 g) as a brown oil.

NMR ($CDCl_3$) δ: 1.77 (4H, m), 2.10 (broad s, $NH_2$), 3.30 (3H, s), 3.40 (2H, t), 4.32 (2H, ABX, $J_{AB}=9$ Hz, $J_{AX}=J_{BX}=H_{H-F}=47$ Hz).

B. 2-Fluoromethyl-2-phthalimido-5-methoxy-valeronitrile

To a solution of 2-fluoromethyl-2-amino-5-methoxy-valeronitrile (1.62 g, 10 mmol) and triethylamine (2.02 g, 20 mmol) in methylene chloride (30 mL), cooled to −20° C., is added phthaloyldichloride (2.03 g, 10 mmol) in methylene chloride (10 mL). The mixture is allowed to warm up to room temperature overnight. After washing with water, 1 N HCl, water again, and drying ($Na_2SO_4$), the solvent is removed under reduced pressure to give 2.4 g (83%) of crude material. This is purified by chromatography on silica (ethyl acetate/petroleum ether 3:7).

NMR ($CDCl_3$): δ2.15 (4H, m), 3.23 (3H, s), 3.40 (2H, t, J=6 Hz), 5.02 (2H, ABX, $J_{AB}=9$ Hz, $J_{AX}=J_{BX}=J_{H-F}=46$ Hz), 7.77 (4H, s).

C. 2-Fluoromethyl-2-phthalimido-5-iodo-valerontrile

2-Fluoromethyl-2-phthalimido-5-methoxy-valeronitrile (1.20 g, 4.14 mmol), trimethylsilyl iodide (3.2 g, 16 mmol) and chloroform (15 mL) are heated to 60° C. under nitrogen for 48 hours. After removal of the solvent, the residue is dissolved in chloroform, washed with water, sodium thiosulfate solution and water again, dried and evaporated to give the crude product as an oil (1.2 g). This is purified by chromatography on silica (ethyl acetate/petroleum ether 1:3) to give pure 2-fluoromethyl-2-phthalimido-5-iodo-valeronitrile.

NMR ($CDCl_3$) δ: 2.0 (4H, m), 3.10 (2H, t), 4.90 (2H, ABX, $J_{AB}=9$ Hz, $J_{AX}=J_{BX}=J_{H-F}=46$ Hz), 7.70 (4H, s).

D. 2-Fluoromethyl-2,5-diphthalimido-valeronitrile

2-Fluoromethyl-2-phthalimido-5-iodo-valeronitrile (1.20 g, 3.11 mmol) and potassium phthalimide (0.75 g, 4 mmol) are heated in dimethylformamide (25 mL) to 80° C. for 2 hours. After standing overnight at room temperature, the DMF is removed by vacuum distillation and the residue is dissolved in chloroform and washed with 1 N KOH and water. After drying ($Na_2SO_4$), evaporation gives 2-fluoromethyl-2,5-diphthalimidovalerontrile as a solid.

NMR ($CDCl_3$) δ: 2.17 (4H, m), 3.73 (2H, t) 4.93 (2H, ABX, $J_{AB}=9$ Hz, $J_{AX}=J_{BX}=J_{H-F}=46$ Hz), 7.73 (8H, broadened s).

E. 2,5-Diamino-2-fluoromethyl pentanoic acid

2-Fluoromethyl-2,5-diphthalimido valeronitrile (1.21 g, 3 mmol) is refluxed with conc. hydrochloric acid (20 mL) for 4 days. After standing at room temperature for several hours, phthalic acid is removed by filtration, the filtrate is evaporated, the residue dissolved in 2 N HCl (20 mL) and carefully extracted with ether (5×10 mL). After evaporation, the residue is dried carefully under vacuum (oil pump) overnight. It is dissolved in dry ethanol (7 mL) and, after filtration, propylene oxide (0.3 g, 5 mmol) in ethanol (1 mL) is added to precipitate the monohydrochloride. This is collected after standing overnight at room temperature and recrystallized from water/ethanol to give pure 2,5-diamino-2-fluoromethyl-pentanoic acid, monohydrochloride; m.p. 260° C. (dec), TLC (EtOH/$NH_4OH$ 80/20): 0.18.

NMR ($D_2O$) δ: 1.93 (4H, m), 3.10 (2H, broad t), 4.83 (2H, ABX, $J_{AB}=10$ Hz, $J_{AX}=J_{BZ}=J_{H-F}=46$ Hz).

EXAMPLE 11

Preparation of a Tablet Formulation

One thousand tablets suitable for oral use are prepared in accordance with the following formulation:

|  | Gm. |
|---|---|
| (a) α-Difluoromethylornithine | 500.0 |
| (b) Dicalcium phosphate | 250.0 |
| (c) Methylcellulose, U.S.P. (15 cps) | 6.5 |
| (d) Talc | 20.0 |
| (e) Calcium stearate | 2.5 |

The α-difluoromethylornithine and dicalcium phosphate are mixed well as a dry powder. The resulting powder is granulated using a 7.5% aqueous solution of methylcellulose, passed through a No. 8 screen and carefully dried. The dried granules prepared in this fashion are passed through a No. 12 screen, lubricated with the remaining talc and calcium stearate, and compressed into tablets. Each tablet contains 500 mg of α-difluoromethylornithine and one or more of such tablets are suitable for oral administration k.i.d. to g.i.d.

EXAMPLE 12

Preparation of a Capsule Formulation

One thousand two-piece hard shell capsules suitable for oral use are prepared using the following ingredients:

|  | Gm. |
|---|---|
| (a) α-Amino-α-fluoromethyl-δ-guanidino-valeric acid | 750.0 |
| (b) Lactose, U.S.P. | 100.0 |
| (c) Starch, U.S.P. | 10.0 |
| (d) Talc, U.S.P. | 5.0 |
| (e) Calcium stearate | 1.0 |

All of the finely powdered materials are mixed dry until uniformly dispersed and then filled into hard-shelled gelatin capsules of the appropriate size.

In a similar fashion, one-piece soft gelatin capsules can be prepared in which the above formulation is granulated, slugged or directly compressed into a rotary die or plate mold in which the capsule is to be formed. Alternatively, the above excipients can be omitted and the active ingredients dispensed as a powder directly into the capsule.

Each capsule contains 750 mg of α-difluoromethylornithine and one or more capsules are suitable for oral administration, b.i.d. to q.i.d.

EXAMPLE 13

Preparation of a Slow-Release Layer Tablet

One thousand layered tablets, comprising a slow release layer and a rapid release layer of α-difluoromethylornithine are prepared as follows:

| | Gm. |
|---|---|
| Slow Release Layer | |
| (a) α-Difluoromethylornithine | 300.0 |
| (b) Hydroxypropyl methylcellulose (400 cps) | 100.0 |
| (c) Mannitol | 100.0 |
| (d) Corn starch | 6.0 |
| (e) Zinc stearate | 3.6 |
| Rapid Release Layer | |
| (f) α-Difluoromethylornithine | 500.0 |
| (g) Microcrystalline cellulose | 100.0 |
| (h) Starch | 100.0 |

Using a suitable mixer, the α-difluoromethylornithine, mannitol and hydroxypropyl methylcellulose are mixed well via geometric dilution. The mixture is mixed in a Fitzmill quipped with a No. 000 screen and granulated using a 5% starch paste prepared by addig the corn starch to approximately 115 ml of water. Additional water is added as required to make a suitable granulation. The resulting granulation is wet-screened using a No. 2 screen and tray dried at 40° C. to 50° C. for 8 to 12 hours. The dried granulation is ground and passed through a No. 10 screen. Zinc stearate, which has passed through a No. 20 screen is added to the granulation, mixed well and the resulting slow release granulation reserved for tablet compression.

The α-difluoromethylornithine for the rapid release layer is milled, if necessary, to obtain a powder having the majority of particles in the range of 10 to 150 microns in size. The milled powder, microcrystalline cellulose and starch are mixed well in a Fitzmill equipped with No. 000 screen and the resulting rapid release mixture reserved for tablet compression.

Using a suitable layer press, such as the Manesty Layer Press, the slow release granulation is added to the adjusted die cavity to provide a layer with a weight of 310 mg. The granulation is lightly tamped by subjecting to a precompression stroke and the rapid release layer added to provide a layer having a weight of approximately 500 mg. The rapid release granulation is added to the die cavity and the final compression pressure is adjusted to provide a suitable tablet with a total weight of approximatly 1.2 g.

EXAMPLE 14

Preparation of a Medicated Feed

A feed composition useful in preventing the gestation of rodents can be prepared utilizing commercially available animal feed as follows. One hundred ml of a 10% aqueous solution of α-difluoromethylornithine is sprayed onto 1 kg of commercially available Purina Laboratory Chow (Ralston-Purina, St. Louis, Mo.), containing the following composition analysis of ingredients:

| Crude protein | 23.0% |
|---|---|
| Crude fat | 4.5% |
| Crude fiber | 6.0% |
| Ash | 8.0% |
| Added minerals | 2.5% |

The pelleted mixture, which contains approximately 1% of α-difluoromethylornithine, is fed ad libitum to rodents. In normal adult rats, this corresponds to a daily dosage intake of approximately 1 g/kg of body weight, whereas in normal adult mice, the daily dosage intake is approximately 2.2 g/kg of body weight, based upon their average consumption.

EXAMPLE 15

Fertility of Male and Female Mice after Treatment with α-Difluoromethylornithine Male and female CDA, HAM-ICR albino mice obtained from Charles River, France are employed throughout. The mice, all proven breeders, are randomly divided into four groups, each containing 7 males and 21 females and treated with α-difluoromethylornithine (DFMO) as follows:

Group I: males given saline; females not treated
Group II: males not treated; females given saline
Group III: males given DFMO; females not treated
Group IV: males not treated; females given DFMO.

The α-difluoromethylornithine is dissolved in deionized water at a concentration of 20 mg/ml and treated animals are subcutaneously administered in the intrascapular region either 200 mg/kg of DFMO or saline every six hours. Male animals are treated from day 1 to 15 and females from day 1 to 23.

Males and females are separately housed from day 1 to day 5. On day 5, each male is placed in a cage containing 3 females. From day 5 to 15 (2 oestrus cycles), males and females are housed together. On day 15, males are sacrificed and on day 23, females are sacrificed and the uterus and its contents carefully examined. Fetuses are designated as "developed" or "undeveloped" depending upon whether the placenta could be separated from a fetus (developed).

Sperm motility is measured by expelling the contents of the vas deferens and mixing with two drops of normal saline on a microscope slide. The percentage of sperm which is actively motile is estimated in at least three microscope fields by an operator unaware of the source of the sample. The percentage of actively motile sperm from the saline treated animals is 61±9 (mean±-SEM), M=7, and for the animals treated with DFMO is 60±10, n=7, the difference not being statistically significant.

Table I illustrates the antifertility effect obtained upon administration of α-difluoromethylornithine.

TABLE I

ANTIFERTILITY EFFECT OF α-DIFLUOROMETHYLORNITHINE

| Treatment | Group I Males Saline | Group I Females not Treated | Group II Males not Treated | Group II Females Saline | Group III Males DFMO | Group III Females not Treated | Group IV Males not Treated | Group IV Females DFMO |
|---|---|---|---|---|---|---|---|---|
| Uterine implantations/gravid female | 11.4 ± 0.7 | (18) | 11.8 ± 0.9 | (16) | 12.7 ± 0.6 | (18) | 13.2 ± 0.7 | (13) |
| Viable developed fetuses/gravid female | 6.8 ± 1 | (18) | 6.9 ± 1 | (16) | 8.6 ± 1 | (18) | 0 | (13) |
| Placental weight of viable developed fetuses | 100 ± 3 | (123) | 102 ± 3 | (100) | 96 ± 2 | (155) | — | |
| Resorption nodules/gravid female | 2.9 ± 0.6 | (18) | 3.4 ± 0.7 | (16) | 1.9 ± 0.4 | (18) | 13.2 ± 0.7 | (13) |

These data demonstrate that treatment of male mice for 5 days prior and 10 days subsequent to being placed with female mice did not significantly alter fertility as reflected by the number of viable developed fetuses present and their placental weight. In contrast thereto, the pretreatment of female mice with DFMO for 5 days prior to copulation and throughout two oestrus cycles exhibits a dramatic effect upon the fertility of the female.

EXAMPLE 16

Antifertility Effects of α-Difluoromethylornithine in Drinking Water

Male and female mice similar to those used in the preceeding Example are administered α-difluoromethylornithine (DFMO) in their drinking water and mated. Aqueous solutions of DFMO at concentrations of 0.125%, 0.5% and 2.0% are employed, corresponding to a dosage of about 0.23 g/kg, 0.81 g/kg and 3.27 g/kg of body weight according to the amount of drinking water consumed and the weight of mice used. Control groups received distilled water for drinking. The following Table II illustrates the antifertility effects that are observed.

TABLE II

EFFECTS OF α-DIFLUOROMETHYLORNITHINE IN DRINKING WATER ON MICE

| | Distilled Water (Control) | 0.125% DMFO | 0.5% DFMO | 2.0% DFMO |
|---|---|---|---|---|
| Length of treatment | 23 days | 23 days | 23 days | 23 days |
| Uterine implantations/gravid female | 12.5 0.7 (21) | 12.4 0.3 (21) | 14.4 0.6 (16) | 16.0 1.3 (7) |
| Viable developed fetuses/gravid female | 8.5 1.1 (21) | 8.0 1.1 (21) | 0.8 0.3 (16) | 0 (7) |
| Resorption nodules/gravid female | 2.5 0.4 (21) | 2.5 0.6 (21) | 11.1 1.0 | 16.0 1.3 (7) |

The above results indicate that at a concentration of 0.5%, implanation occurs normally but there are significantly fewer viable developed fetuses and significantly greater resorption of nodules per gravid female. At a concentration of 2% DFMO, the number of implantations were normal, however these were mainly resorption nodules and no viable developed fetuses are present.

What is claimed is:

1. A method of preventing gestation in mammals which comprises the administration to said mammals of a contragestationally effective amount of a compound of the formula:

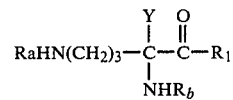

wherein:

Y is FCH$_2$—, F$_2$CH—, or F$_3$C—;

R$_a$ and R$_b$ are, independently, hydrogen, (C$_1$–C$_4$)alkylcarbonyl, or the group

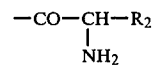

wherein R$_2$ is hydrogen, (C$_1$–C$_4$) alkyl, benzyl, or p-hydroxybenyl;

R$_1$ is hydroxy, (C$_1$–C$_8$) alkoxy, the group —NR$_4$R$_5$, wherein R$_4$ and R$_5$ are, independently, hydrogen, or, (C$_1$–C$_4$)alkyl, or the group

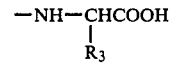

wherein R$_3$ is hydrogen, (C$_1$–C$_4$) alkyl, benzyl, or p-hydroxybenzyl; and the pharmaceutically acceptable salts and individual optical isomers thereof.

2. A method as defined in claim 1 wherein Y is —CH$_2$F or —CHF$_2$.

3. A method as defined in claim 1 or 2 wherein R$_1$ is hydroxy.

4. A method as defined in claim 1 or 2 wherein R$_1$ is hydroxy and R$_a$ is hydrogen.

5. A method as defined in claim 1 or 2 wherein R$_1$ is hydroxy and R$_b$ is hydrogen.

6. A method as defined in claim 1 or 2 wherein R$_a$ and R$_b$ are hydrogen.

7. A method as defined in claim 2 which comprises the administration of 2,5-diamino-2-fluoromethylpentanoic acid.

8. A method as defined in claim 2 which comprises the administration of 2,5-diamino-2-diamino-2-difluoromethylpentanoic acid.

* * * * *

UNITED STATES PATENT AND TRADEMARK OFFICE
CERTIFICATE OF CORRECTION

PATENT NO. : 4,309,442
DATED : January 5, 1982
INVENTOR(S) : Philippe Bey; Michel Jung It is certified that error appears in the above-identified patent and that said Letters Patent is hereby corrected as shown below:

At Column 2, Line 67, the patent reads "intented" and should read --intended--.

At Column 4, Line 29, the patent reads "Tables B 26-27" and should read ---Tables 26-27--.

At Column 5, Line 49, the patent reads "$R_{11}CNH\text{-}(CH_2)_3$" and should read $$R_{11}\overset{\overset{O}{\|}}{C}NH\text{-}(CH_2)_3$$

At Column 6, Line 11, the patent reads "I necessary" and should read -- I is necessary--.

At Column 10, Line 66, the patent reads "mamal" and should read --mammal--.

At Column 11, Line 6, the patent reads "practise" and should read --practice--.

At Column 12, Line 54, the patent reads "suspention" and should read --suspension--.

At Column 13, Line 32, the patent reads "saturated chloride" and should read --saturated sodium chloride--.

At Column 15, Line 28, the patent reads "additioal" and should read --additional--.

At Column 16, Line 52, the patent reads "is 1 g of triethylamine" and should read --of 1 g of triethylamine--.

UNITED STATES PATENT AND TRADEMARK OFFICE
CERTIFICATE OF CORRECTION

PATENT NO. : 4,309,442

DATED : January 5, 1982

INVENTOR(S) : Philippe Bey; Michel Jung

It is certified that error appears in the above-identified patent and that said Letters Patent is hereby corrected as shown below:

At Column 18, Line 20, the patent reads "$J_{AX} = J_{BZ}$" and should read --$J_{AX} = J_{BX}$--.

At Column 19, Line 31, the patent reads "quipped with" and should read --equipped with--.

At Column 19, Line 32, the patent reads "addig" and should read --adding--.

At Column 21, Line 42, the patent reads "0.125% DMFO" and should read --0.125% DFMO--.

At Column 22, Line 23, the patent reads "alkylcarbonyl," and should read --alkycarbonyl,--

At Column 22, Line 31, the patent reads "p-hydroxybenyl" and should read --p-hydroxybenzyl--.

Signed and Sealed this

Second Day of January, 1990

Attest:

JEFFREY M. SAMUELS

*Attesting Officer*   *Acting Commissioner of Patents and Trademarks*